United States Patent [19]

Morgan

[11] Patent Number: 4,739,437
[45] Date of Patent: Apr. 19, 1988

[54] PACEMAKER OUTPUT SWITCH PROTECTION

[75] Inventor: Wayne A. Morgan, Los Angeles County, Calif.

[73] Assignee: Siemens-Pacesetter, Inc., Sylmar, Calif.

[21] Appl. No.: 921,701

[22] Filed: Oct. 22, 1986

[51] Int. Cl.[4] .............................................. H02H 3/14
[52] U.S. Cl. ........................................ 361/88; 361/91; 361/58; 357/48; 357/23.13
[58] Field of Search ...................... 361/58, 77, 91, 88; 357/48, 86, 23.13; 307/246, 254; 128/419 PG

[56] References Cited

U.S. PATENT DOCUMENTS 4,496,849 1/1985 Kotowski ............................. 307/254

OTHER PUBLICATIONS

COS/MOS Quad Bilateral Switch, CD4066A types, "RCA COS/MOS Intergrated Circuits," p. 519 (1977 RCA Corporation).

Primary Examiner—A. D. Pellinen
Assistant Examiner—Todd E. DeBoer
Attorney, Agent, or Firm—Bryant R. Gold

[57] ABSTRACT

A protected output switch for an implantable medical device, such as a pacemaker, is disclosed. Through this output switch, a stimulation pulse is delivered from an internal storage element to an output terminal. The output switch includes a first N-channel MOSFET switch having its source terminal connected to the internal storage element and its drain terminal connected to the output terminal. The gate terminal of the N-channel MOSFET switches is connected to approriate logic switching signals. Included as part of the output switch is a second N-channel MOSFET switch having its source terminal connected to the P-well terminal of the first N-channel MOSFET switch, its drain terminal connected to the internal storage element, and its gate terminal connected to the output terminal. This second switch serves to block any potentials, whether internal or external, from being applied to the base of a parasitic NPN bipolar transistor that exists within the output switch. Should such NPN bipolar transistor be turned on, large potentially destructive currents could flow through the output switch.

10 Claims, 3 Drawing Sheets

PACEMAKER OUTPUT SWITCH PROTECTION

BACKGROUND OF THE INVENTION

The present invention relates to implantable pacemakers, and more particularly to the output switch configuration used in an implantable pacemaker. Even more particularly, the present invention relates to an output switch for a pacemaker that includes built-in protection means for preventing undesirable transient currents from flowing therethrough whenever the output line of the pacemaker is subjected to a more negative potential than a stored stimulation potential.

The function of a pacemaker is to provide a stimulation pulse to a desired location in or on the heart whenever the heart needs to contract. Modern pacemakers allow the amplitude of the stimulation pulse to be programmably controlled. The desired amplitude of the stimulation pulse is stored within a storage element inside of the pacemaker, typically a capacitor. At the appropriate time this storage element is switchably connected through an output switch to an output terminal of the pacemaker. The output terminal of the pacemaker, in turn, is connected to the desired location of the heart by means of a suitable conductive lead. This lead has at its distal end an electrode tip through which the stimulation pulse is presented to the heart tissue or fluids. A suitable electrical return path from the heart back to the pacemaker is also provided either through the conductive body tissue and fluids back to the pacemaker case (unipolar pacing) or through a ring electrode positioned on the pacemaker lead near the electrode tip (bipolar pacing).

The output switch that is used to switchably connect the storage element to the output terminal of the pacemaker comprises a semiconductor solid state switch. In recent years, such switches have employed metal oxide semiconductor field effect transistor (MOSFET) devices. (For purposes of this application, the term "MOSFET" will be used to broadly describe all types of semiconductor switches wherein an applied gate voltage selectively inhibits or enhances a conductive channel between source and drain terminals.) MOSFET type switches are generally preferred over other types of semiconductor switches, such as bipolar transistors, because of their low power consumption. That is, a MOSFET switch device consumes power only during the transition from an ON to an OFF state, or from an OFF to an ON state. In contrast, a bipolar switch typically consumes power continuously while in an ON state. Further, MOSFET type devices are more compatible with, and in fact can be employed as part of, the complementary metal oxide semiconductor (CMOS) circuits that comprise the digital logic circuits of a modern pacemaker. That is, the output switch is advantageously realized using the same type of semiconductor switches that are used within the digital and analog portions of the pacemaker, thereby allowing the switch to be fabricated as part of the same semiconductor chip (on the same semiconductor substrate) as the other pacemaker circuits. This sharing of the semiconductor substrate allows the pacemaker circuits to be realized in a smaller space, thereby allowing the overall pacemaker to be smaller in size.

Unfortunately, the fabrication of MOSFET devices on a semiconductor substrate often results in the existence of parasitic bipolar transistors within the same substrate. (As used herein, the term "parasitic" refers to an unwanted circuit element that is an unavoidable adjunct of a wanted circuit element. That is, the bipolar transistor is an unwanted circuit element that is an unavoidable adjunct of a wanted circuit element—the MOSFET device.) The presence of a parasitic bipolar transistor can cause many problems. For example, a typical MOSFET configuration provides the equivalent of a bipolar PNP and NPN parasitic transistors, configured in an arrangement that is equivalent to a silicon controlled rectifier (SCR). This equivalent SCR, is triggered, can cause the substrate to become "latched" and inoperable. Accordingly, precautions must be taken in order to prevent any parasitic SCR configurations from triggering and latching.

The output switch circuits of modern pacemakers comprise suitable N-channel and P-channel MOSFET devices. With the use of such devices there also exists a parasitic NPN transistor having its collector coupled to the supply voltage $V_{DD}$ of the pacemaker, its emitter connected to the output line of the pacemaker, and its base connected to the stored stimulation voltage, SSV, of the pacemaker. Depending upon whether the storage element holding the stored stimulation charge is fully charged or discharged, the potential actually applied to the base of the parasitic transistor may vary between $V_{DD}$ and SSV. In any event, if the output line of the pacemaker is subjected to a potential that is lower than the potential applied to the base of the parasitic transistor, the bipolar NPN transistor will turn ON. When the bipolar transistor turns ON in this fashion, it connects the supply voltage, $V_{DD}$, to the output line through its collector and emitter terminals. This action further connects the stored stimulation voltage, SSV, to the output line through the base-emitter terminals of the bipolar transistor. Thus, any potential on the output line that is lower than SSV turns this NPN parasitic bipolar transistor ON, thereby causing large currents to flow from $V_{DD}$ and/or SSV to the output terminal. Such large output currents, even if only transient in nature, can potentially damage the output switching circuitry. Moreover, the flow of such currents needlessly depletes the limited energy of the pacemaker's battery.

Attempts have been made in the prior art to limit the magnitude of any such large transient currents that might flow when a negative potential appears on the output line. However, such current limiting devices typically require the use of additional discrete components, which additional discrete components not only add to the bulk and expense of the pacemaker, but their effectiveness at limiting the magnitude of the transient currents may be dependent upon the magnitude of the triggering negative potential appearing on the output line of the pacemaker. Hence, whereas such limiting devices may be effective at limiting the value of the transient currents to less than destructive values when a nominal negative potential appears on the output line, they may not be effective when a greater than normal negative potential appears on the output line. Further, even if such limiting devices prevent the transient currents from reaching destructive amplitudes, they do not prevent the needless depletion of the pacemaker's battery.

Unfortunately, it is not uncommon for the output line of the pacemaker to have applied thereto a potential that is lower than the the stored stimulation voltage, SSV. The most common situation where this might occur would be the application of a defibrilation pulse or pulses to the patient wearing the pacemaker. Numerous other external factors could also cause the output line to go sufficiently negative to turn the parasitic transistor ON. Further, in addition to these external sources of a negative turn-on potential, it is also possible for internal sources of a negative potential to turn the parasitic transistor ON. Hence, both external and internal sources of a negative potential can possibly trigger potentially destructive transient currents within the output switching circuitry. Accordingly, there is a need in the pacemaker art for preventing such transient currents from flowing in the output switch circuitry in the event that the output line of the pacemaker is subjected to a negative potential, either from internal or external sources.

SUMMARY OF THE INVENTION

The present invention prevents, not just limits, transient currents from flowing through the output switching circuits of a pacemaker when the output line of the pacemaker goes more negative than the stored stimulation voltage, SSV. This condition (of the output line going more negative than SSV) is especially likely to occur during defibrilation, but could also occur at other times.

As described previously, the output switch of an implanted pacemaker switchably connects the stored stimulation voltage, SSV, to the output terminal of the pacemaker. The output terminal, in turn, is connected in conventional manner, via a suitable lead, to a desired stimulation location in or on the patient's heart. The output switch comprises at least an N-channel MOSFET device. (A P-channel MOSFET device is sometimes optionally used in parallel with the N-channel device.) Unfortunately, a parasitic NPN bipolar transistor results from the fabrication of such an N-channel MOSFET switch. The bipolar parasitic transistor may disadvantageously turn ON whenever the output terminal is subjected to a voltage lower than SSV. Such turn-on action allows potentially damaging transient currents to flow from $V_{DD}$ or SSV to the lower potential output line.

The output switch configuration of the present invention advantageously prevents such transient currents from flowing by preventing the parasitic bipolar transistor from turning ON. This is accomplished by inserting a blocking MOSFET switch in the base of the parasitic bipolar transistor. The blocking MOSFET switch is opened whenever the output line goes lower in potential than SSV, which is likely to occur when a defibrilation pulse is applied to the patient's chest.

It is a feature of the present invention to prevent, not just limit, transient currents from flowing through the output switching circuitry of a pacemaker whenever the output line of the pacemaker is momentarily subjected to a lower voltage potential than a stored stimulation voltage. A related feature of the invention prevents such transient currents from flowing through the output switching circuitry whenever the output line of the pacemaker is subjected to a lower voltage potential than the stored stimulation voltage regardless of the magnitude of the lower potential applied to the output line.

It is another feature of the present invention to provide output switch protection for an implanted pacemaker using components that form an integral part of the same semiconductor substrate as the output switching circuitry and other pacemaker circuits without the need of additional discrete components.

Yet another feature of the invention provides a MOSFET control switch in the output switch circuitry of a pacemaker that switchably blocks the base terminal of a parasitic bipolar transistor present in the output switch circuitry from receiving any base current, thereby preventing such bipolar transistors from turning ON. A still further feature prevents such parasitic bipolar transistor present in the output MOSFET switching circuitry from turning ON whenever the pacemaker's output line goes lower in potential than a stored stimulation voltage.

BRIEF DESCRIPTION OF THE DRAWINGS

The above and other features and advantages of the present invention will be more apparent from the following more particular description thereof, presented in conjuction with the following drawings, wherein.

DETAILED DESCRIPTION OF THE INVENTION

The following description is of the best presently contemplated mode of carrying out the invention. This description is not to be taken in a limiting sense but is made merely for the purpose of describing the general principles of the invention. The scope of the invention should be determined with reference to the appended claims.

It is noted that in the description that follows, and more particularly when reference is made to the drawings, that like numerals are used to describe like parts throughout.

Figure 1:
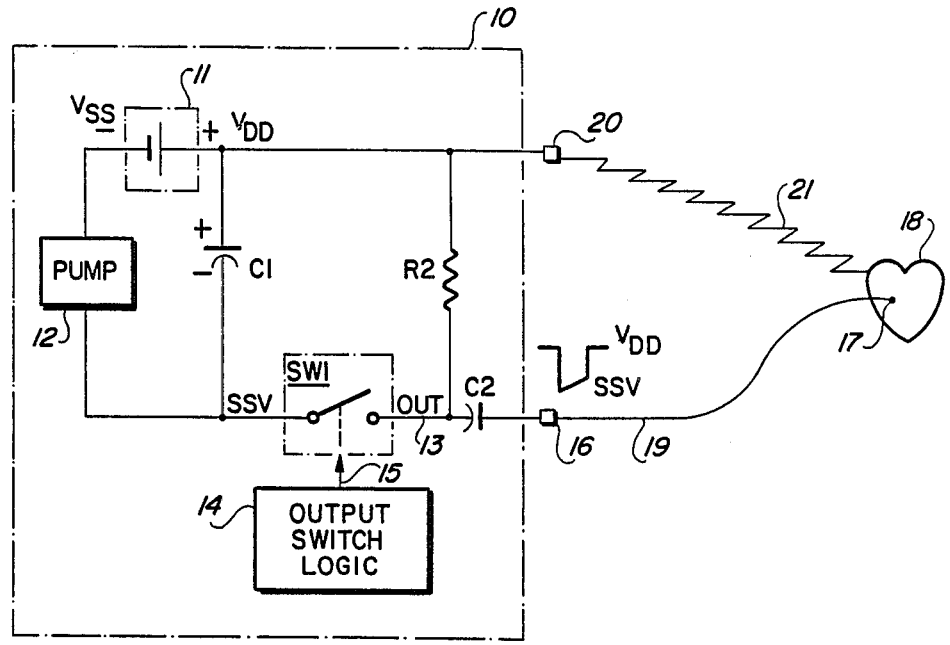
FIG. 1 is a simplified schematic/block diagram of the output switch configuration of an implanted pacemaker.

Referring first to FIG. 1, there is shown a simplified schematic/block diagram of the output switch configuration 10 of an implanted pacemaker. In general, the output switch circuitry 10 includes a battery 11, a positive terminal of which is designated as $V_{DD}$, and the negative terminal of which is designated as $V_{SS}$. In the usual configuration, the positive terminal $V_{DD}$ on the battery 11 is connected to a reference electrode 20 of the pacemaker. A storage capacitor C1 is connected between the positive battery terminal $V_{DD}$ and switch SW1. A charge pump circuit 12 is connected between the negative terminal $V_{SS}$ of battery 11 and switch SW1. It is the function of the charge pump 12 to place a charge on the capacitor C1 equal to the stimulation potential that is to be delivered to the patient's heart 18. This charge may be greater than $V_{SS}$ due to voltage multiplying techniques used within the charge pump circuit 12. The charge pump circuit 12 may be of conventional design. The charge or potential that is stored on capacitor C1 is designated in the figures as the stored stimulated voltage, SSV.

When it is desired to deliver a stimulation pulse to the heart 18, the switch SW1 closes in response to a control signal delivered on signal line 15 from output switch logic 14. Closure of switch SW1 allows the stored stimulation voltage to be connected to the output signal line 13. Thus, the SSV side of capacitor C1 may be viewed as a source node, and output line 13 may be viewed as a destination node, with switch SW1 connecting the source node to the destination node in response to a control signal.

The output signal line 13 is coupled through coupling capacitor C2 to the pacemaker output terminal 16. A suitable pacemaker lead 19 is connected to the output terminal 16. The lead 19 is positioned on or in a desired location of the heart 18. At the distal end of the lead 19 is an electrode tip 17 which is in electrical contact with the heart tissue or fluids. Thus, when switch SW1 is closed, the stored stimulation voltage SSV is delivered through output signal line 13, coupling capacitor C2, output terminal 16, and lead 19 to the electrode tip 17. An electrical return path 21 to a reference terminal 20 of the pacemaker is provided either by the conductive body tissue or fluids, if a unipolar pacing lead is employed, or by a ring electrode (not shown) if a bipolar pacing lead is employed. Any charge remaining on coupling capacitor C2 as a result of current flow from terminal 16 to terminal 20 is bled off by resistor R2. Thus, the voltage on C2 is restored to the same value as prior to closure of switch SW1.

It is thus apparent from FIG. 1 that the stimulation pulse provided at the output terminal 16 is a negative pulse having a reference level of $V_{DD}$ and a magnitude of SSV. Such a system is often referred to as a "positive ground" system inasmuch as the positive terminal $V_{DD}$ of the battery 11 is utilized as the reference potential for operation of the electrical circuits within the output switch configuration 10.

Figure 2:
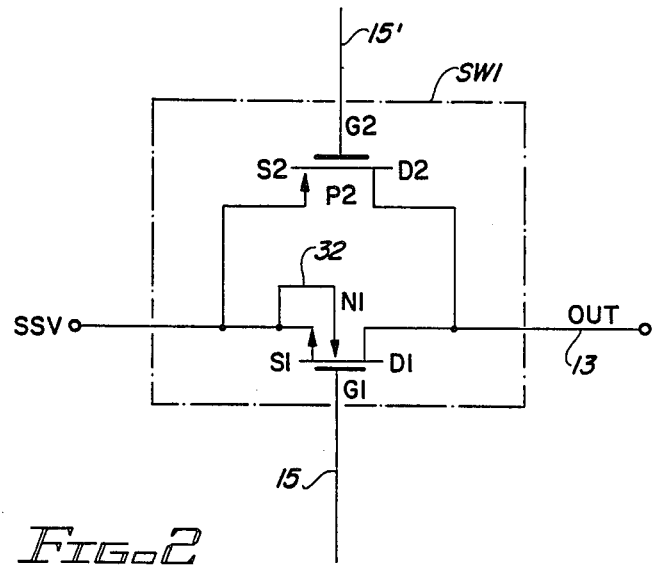
FIG. 2 is a schematic diagram of the MOSFET output switch SW1 of FIG. 1.

Referring next to FIG. 2, there is shown a schematic diagram of the output switch SW1 as has been commonly used in prior art devices. The switch configuration includes an N-channel MOSFET switch N1 in parallel with an optional P-channel MOSFET switch P2. The source terminal S1 of the switch N1 is connected to the source terminal S2 of switch P2. Similarly, the drain terminal D1 of N1 is connected to the drain terminal D2 of switch P2. The gate terminal G1 of switch N1 is connected to the output switch logic 14 via signal line 15. Similarly, the gate terminal G2 of switch P2 is connected to the output switch logic 14 by an appropriate signal line 15'. (The control signal on signal line 15' is of the opposite polarity as the control signal on signal line 15.) In operation, it is desired that both switch N1 and P2 be ON at the same time. The N-channel switch N1 is used to pass the higher magnitude SSV potentials, while the P-channel switch P2 is used to pass the lower magnitude SSV potentials.

Figure 3A:
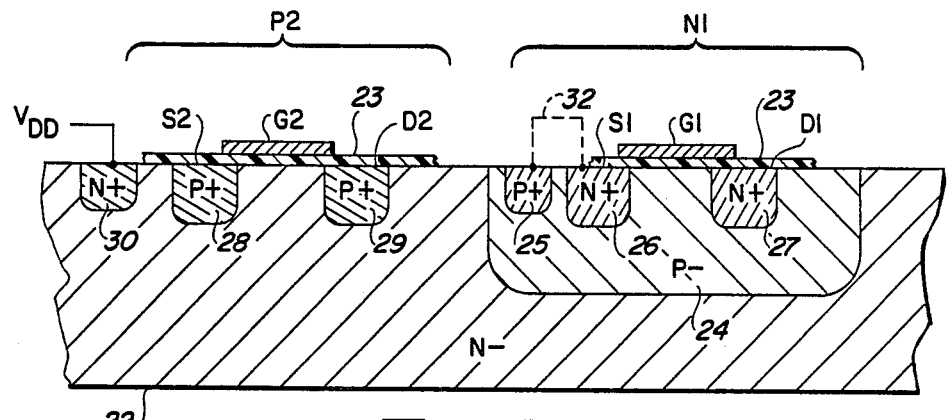
FIG. 3A is a simplified cross-sectional view of an N-channel MOSFET device and a P-channel MOSFET device fabricated on the same substrate.

Referring next to FIG. 3A, there is shown a simplified cross sectional view of a semiconductor substrate 22 on which the MOSFET switches N1 and P2 have been fabricated. The substrate 22 is doped with N− carriers. The switch P2 is fabricated within this N− doped substrate by selectively creating regions 28 and 29 that are doped with P+ carriers. As indicated in FIG. 3A, region 28 functions as the source S2 of switch P2, while region 29 functions as the drain P2 of switch P2. A metal oxide insulating layer 23, only a portion of which is shown in FIG. 3A, is then deposited over the surface of the substrate 22. A metal or polysilicon gate layer G2 is then deposited over the insulating layer 22 so as to be over the substrate region lying between the P+ region 28 and the P+ region 29. When a negative voltage is applied to gate G2 (relative to the potential of the substrate 22), a region or channel of P+ carriers is enhanced between the source and drain terminals 28 and 29. This enhanced P-channel allows current to flow from the source S2 to the drain D2 (or, depending upon the polarity of the potential applied between S1 and D1, from the drain D2 to the source S2). Hence, this type of switch is referred to as a P-channel device because a P-channel is enhanced therein upon application of a proper polarity gate voltage, thereby allowing current to flow between the source and drain terminals.

In order to fabricate an N-channel switch in a N− substrate, it is first necessary to create a P-well 24 within the substrate 22. This is done by doping the region 24 with P-carriers. Within this P-well 24, regions 26 and 27 are created having N+ carriers doped therein. The region 26 functions as the source terminal S1, and the region 27 functions as the drain terminal D1, of the switch N1. After the oxide insulating layer 23 is deposited over the P-well 24, a metal or polysilicon gate layer G1 is deposited over the region between the N+ regions 26 and 27. A positive voltage applied to the gate G1 enhances an N-channel between the regions 26 and 27, thereby allowing current to flow therebetween.

Not shown in FIG. 3A are the metal interconnect lines that are used to electrically connect the regions of the semiconductor in order to form a working circuit. However, conventional techniques can be used to realize such interconnections, including the vias that must pass through the insulating layer 23 in order to electrically contact desired regions of the device. Included in FIG. 3A is an N+ region 30 to which the positive battery terminal $V_{DD}$ is connected, and a P+ region 25. The P+ region 25 provides a means for making electrical connection with the P-well 24.

Figure 3B:
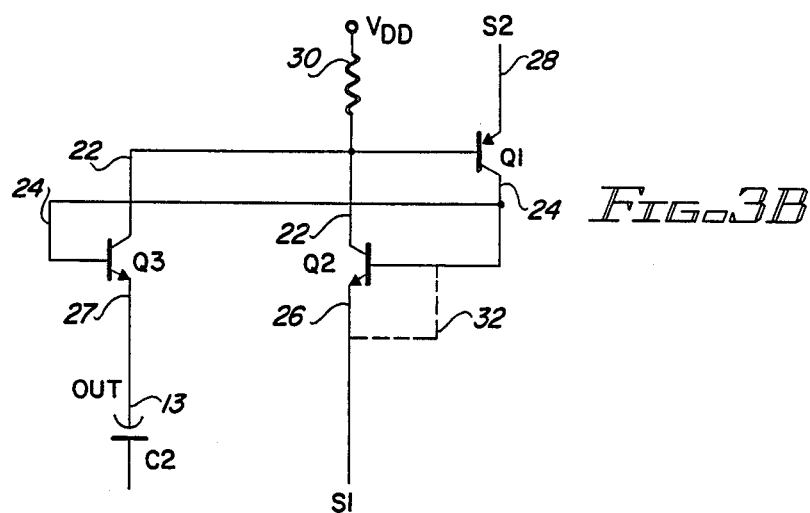
FIG. 3B is a schematic diagram illustrating how the PNPN configuration of FIG. 3A can result in an equivalent SCR comprised of PNP transistor Q1 and NPN transistor Q2, which SCR could latch and draw large destructive currents.

As indicated previously, the creation of MOSFET devices, such as switches N1 and P2, also creates parasitic bipolar transistors. For example, the P+ region 28, the N− substrate 22, and the P− region (P-well) 24 can function as a PNP bipolar transistor Q1 as shown in FIG. 3B. Similarly, the N− substrate 22, the P-well 24 and the N+ region 26 or the N+ region 27 can function as NPN transistors Q2 and Q3 (as shown in FIG. 3B). The base of bipolar transistor Q1 is coupled to $V_{DD}$ through an effective resistance 30' (caused by the N+ region 30). This resistance 30' is typically a very small resistance. As indicated in FIG. 3B, the PNP transistor Q1 and the NPN transistor Q2 are configured as a silicon controlled rectifier (SCR). In an SCR configuration, any current that begins to flow in either Q1 or Q2 operates to turn both transistors on in a latched condition. If this occurs, the supply potential $V_{DD}$ is effectively latched to the stored stimulation voltage point SSV, which point is connected to S1. Such latching can draw large destructive currents from $V_{DD}$ to SSV (destructive in the sense that the semiconductor devices and/or interconnecting metal could be damaged and become inoperable). In order to prevent an SCR configuration of the type shown in FIG. 3B, the N+ region 26 (serving as the source S1 of switch N1) is electrically connected to the P-well 24 by way of conductor 32. This has the effect of clamping the base of transistor Q2 (FIG. 3B) to the emitter of Q2, thereby preventing Q2 from turning ON.

As further indicated in FIG. 3B, a second NPN transistor Q3 is also created by the fabrication of the MOSFET switch N1. This NPN transistor Q3 has as its collector the N− substrate 22. Its base is the P-well 24, and its emitter is the N+ region 27, which emitter is also the drain terminal D1 of switch N1. Unfortunately, it is not possible to clamp the base 24 of transistor Q3 to emitter 27 as was done with Q2. To do so would effectively connect the stored stimulation voltage, SSV, to the output line 13, thereby effectively shorting switch SW1.

Figure 4:
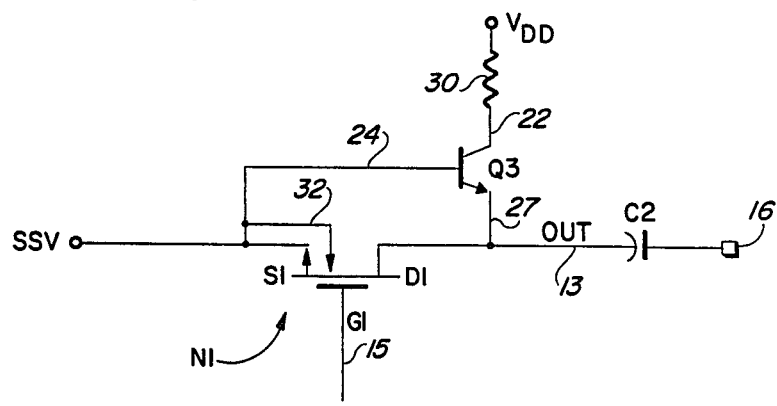
FIG. 4 is a schematic diagram of the N-channel MOSFET output switch and the equivalent parasitic NPN transistor Q3 that remains even after the equivalent parasitic NPN transistor Q2 of FIG. 3B has been clamped OFF with connection 32.

To explain how the parasitic transistor Q3 may still cause problems, reference is made to FIG. 4. In FIG. 4 a schematic diagram of the N-channel switch N1 and the parasitic transistor Q3 is shown. As is evident from FIG. 4, and as also can be determined from FIG. 3A and FIG. 3B, the base of parasitic transistor Q3 is connected to the source terminal S1 of N-channel switch N1. The emitter 27 of parasitic transistor Q3 is connected to the drain terminal D1 of N-channel switch N1, which in turn is connected to the output line 13. The collector 22 of parasitic transistor Q3 is coupled to the supply voltage $V_{DD}$ through the N+ region 30.

In operation, if the output terminal 16 (FIG. 4) of the pacemaker has a negative voltage applied thereto, such as might occur during defibrilation or during dual chamber pacemaker operation where the other channel's output pulse provides the negative voltage, such negative voltage is momentarily coupled through capacitor C2 and appears on output line 13. If the voltage on output line 13 is below the stored stimulation voltage appearing at the base of transistor Q3, then transistor Q3 turns ON, thereby allowing large currents to flow from $V_{DD}$ through Q3 to the output line 13. Moreover, current can also flow from SSV through the base-emitter junction of Q3 to the output line 13. These currents can potentially be of sufficient magnitude to cause damage to the MOSFET device N1, thereby rendering the output switch of the pacemaker inoperable. Further, these currents needlessly deplete the limited stored energy of the pacemaker.

In dual chamber pacemakers, the above-described problem (of applying a negative voltage to the pacemaker output terminal) is especially noticeable. Dual chamber pacemakers employ two channels, designated, for purposes here, as channel A and channel B. Each channel has an output circuit substantially as shown in FIG. 1. If the output pulse amplitude of channel A (SSV of channel A) is much lower than the pulse amplitude of channel B, the channel B output switch may conduct (close) during delivery of the channel A output pulse, thereby causing unwanted current to flow through electrode B. Such action not only needlessly depletes the limited storage energy of the pacemaker, but can also cause an unwanted tissue stimulation of the area (chamber of the heart) where electrode B is located.

Figure 5:
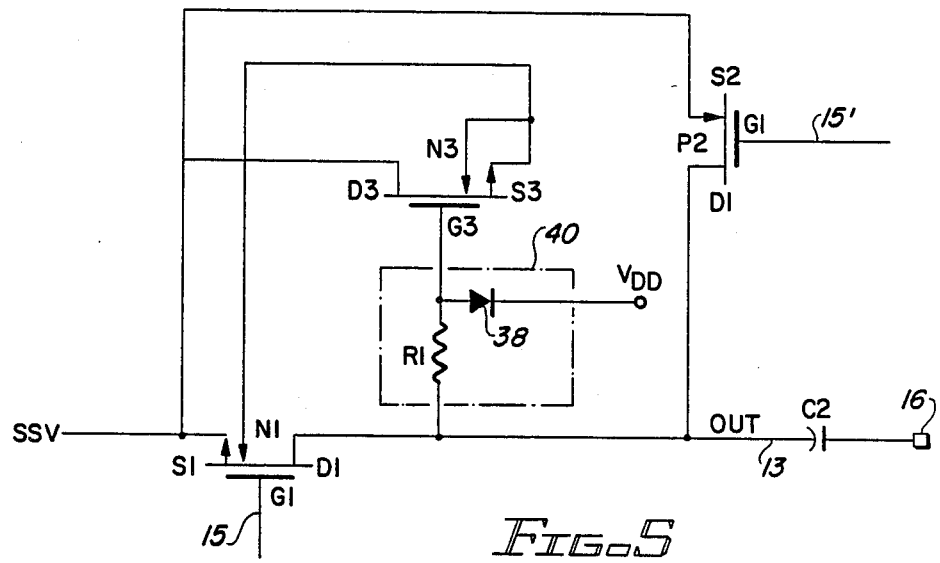
FIG. 5 is a schematic diagram of the pacemaker output switch of the present invention.

Referring next to FIG. 5, a schematic diagram of the output switch of the present invention is shown. This output switch configuration includes the N-channel switch N1 in parallel with the P-channel switch P2 as in FIG. 2. In addition, there is included a second N-channel switch N3 having its drain terminal D3 connected to the source terminal S1 of the switch N1. The source terminal S3 of the switch N3 is connected to the P-well terminal of switch N1. Normally, as shown in FIG. 2 and FIG. 4, the P-well terminal is connected to the source terminal S1 by an appropriate electrical connection 32. (Note, that in a schematic representation, the P-well terminal of an N-channel device is depicted as an arrow pointing towards the line connecting the S1 and D1 terminals. This arrow is typically positioned adjacent to the S1 terminal.) As discussed above, this connection prevents an SCR from being formed from the parasitic bipolar transistors, and thus prevents latchup from occurring. In accordance with the present invention, however, the P-well of the N-channel switch N1 is not connected to the source S1. Rather, as shown, it is connected to the source S3 of the additional N-channel switch N3. (It is noted that the P-well of the N-channel switch N3 is connected, as usual, to the source terminal S3.) The gate G3 of switch N3 is connected through a resistor R1 to the output line 13. A diode 38 is also provided from the output line 13 to the positive supply voltage $V_{DD}$. This diode 38 serves to protect the thin oxide insulating layer (layer 23 in the figures) of N3 from destructive breakdown. The resistor R1 and diode 38, hereafter referred to as gate protection circuit 40, can be realized using hybrid or monolithic techniques.

Figure 6:
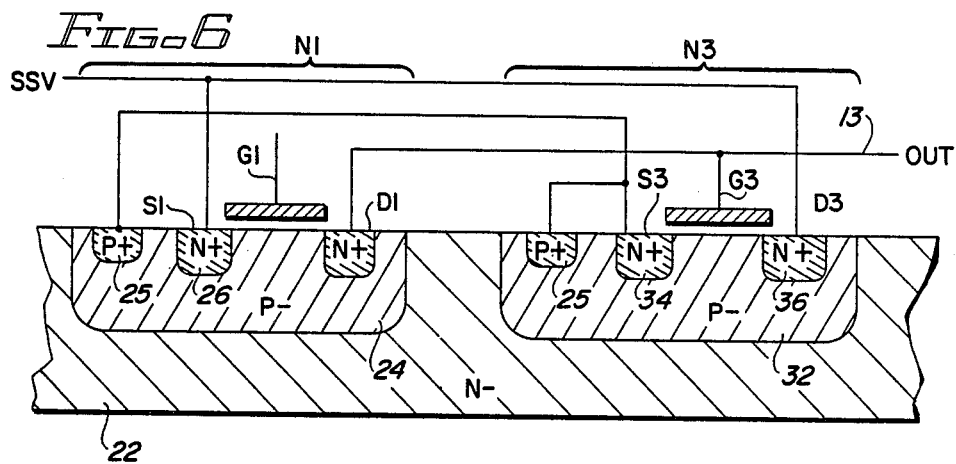
FIG. 6 is a simplified cross-sectional view of the substrate on which the N-channel switches used in the output switch of FIG. 5 are fabricated.

Referring next to FIG. 6, a partial cross-sectional view of the output switch of the present invention is shown. FIG. 6 includes the two N-channel switches N1 and N3, and the various interconnections that are made therebetween. (not shown is the P-channel switch P2.) Basically, the additional N-channel switch N3 is realized by inserting an additional P-well 32 into the N− substrate 22. Within the P-well 32, two additional N+ regions 34 and 36 are placed to function as the source S3 and the drain D3. The gate G3 is then realized in conventional manner by placing a metal or polysilicon layer above the region on the P-well 32 between the N+ regions 34 and 36. (Not shown in FIG. 6, but understood to be a part thereof, is the oxide insulating layer that electrically insulates the gates G1 and G3 from their respective P-wells, source regions, and drain regions.) Also, it is noted that the two N-channel switches N1 and N3 could be fabricated in the same P-well.

Figure 7:
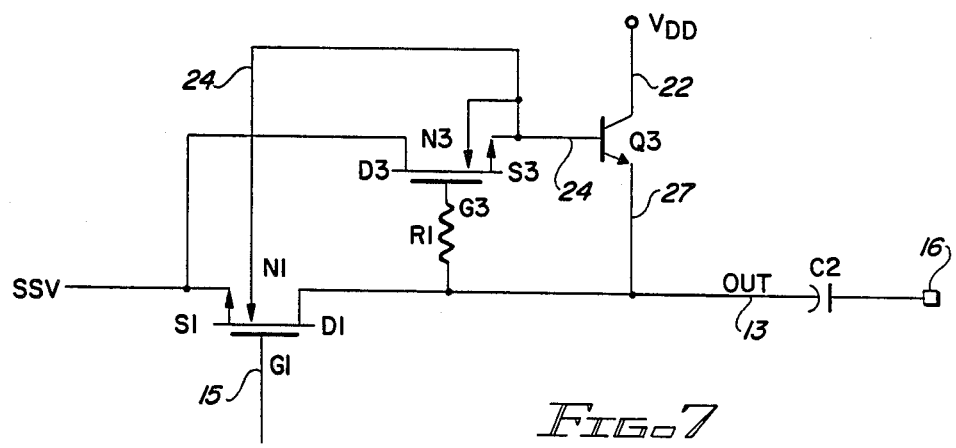
FIG. 7 is a schematic diagram of the N-channel portion of the output switch of FIG. 5, including the equivalent parasitic bipolar NPN transistor Q3.

A schematic diagram of the output switch configuration of FIG. 5, including the parasitic bipolar transistor Q3, is depicted in FIG. 7. As is evident from FIG. 7, the additional N-channel switch N3 is inserted so as to control the base current delivered to transistor Q3. Advantageously, the switch N3 opens whenever the output line 13 goes negative. This happens because the negative voltage appearing on the output line 13, from whatever source (external or internal) is coupled through resistor R1 to gate G3. Because switch N3 is an N-channel MOSFET device, it turns OFF when a negative voltage is applied to the gate thereof. With the base circuit of transistor Q3 open in this manner, it cannot turn on when the output line 13 goes negative. Thus, no potentially destructive transient currents can flow from $V_{DD}$ to the output line 13. Moreover, with the switch N3 open, there is no path provided through which a current from the stored stimulation voltage SSV can flow through the base-emitter junction of Q3 to the output line 13. Thus, the blocking switch N3 prevents the parasitic transistor Q3 from turning ON, and thereby prevents undesired transient currents from flowing in the output switch circuits.

It is noted that when the output line 13 is high—when it is near $V_{DD}$—that transistor N3 is ON. Thus, the equivalent circuit configuration when the output line 13 is high is essentially that shown in FIG. 4. However, as soon as the output line starts to go more negative than SSV, the N-channel switch N3 opens, thereby preventing or blocking any currents from flowing through the parasitic transistor Q3.

Advantageously, while the present invention includes an additional N-channel switch, such switch can readily be realized as an integral part of the same semiconductor substrate from which the other MOSFET devices used within the pacemaker are realized. Significantly, no additional discrete components are required, with the possible exception of resistor R1 and diode 38, which may be realized using discrete components. However, resistor R1 and diode 38 comprise a gate protection circuit 40 which can readily be realized in the same manner as are other gate protection circuits used for various other functions within the pacemaker circuits.

It is further noted that with parasitic transistor Q3 having its base terminal opened by switch N3 that all current flowing through Q3 is prevented, not just limited in magnitude. This represents a significant improvement over the prior art where attempts were made to limit to nondestructive values the amount of current that could flow.

While the invention disclosed herein has been described by means of a specific embodiment and application thereof, numerous modifications and variations could be made thereto by those skilled in the art without departing from the spirit and scope of the present invention. For example, the invention has been described with reference to N-channel devices formed on a N-substrate (thereby requiring the use of P-wells in order to realize the N-channel devices). The principles of the invention apply equally well to P-channel devices formed on a P-substrate (thereby requiring the use of N-wells in order to realize the P-channel devices). Similarly, the principles of the invention apply to any configuration wherein parasitic devices result that can cause undesired performance. It is therefore to be understood that within the scope of the appended claims, the invention may be practiced otherwise than as specifically described herein.

What is claimed is:

1. An output switch serving to electrically connect a source node within a medical device to a destination node within said medical device in response to a control signal, said output switch including:
    a first MOSFET switch formed in a first well region of a first polarity type within a substrate of a second polarity type, said first MOSFET switch having a first source terminal, a first drain terminal, a first gate terminal, and a first well terminal, said source terminal being connected to said source node, said drain terminal being connected to said destination node, said gate terminal being coupled to said control signal, and said first well terminal being connected to said first well region; and
    a second MOSFET switch formed in a second well region of the first polarity type having a second source terminal, a second drain terminal, a second gate terminal, and a second well terminal, the second drain terminal being electrically connected to the first source terminal, the second source terminal being electrically connected only to the first and second well terminals, the second well terminal being connected to said second well region and the second gate terminal being electrically coupled to the first drain terminal.

2. The output switch of claim 1 further including a third MOSFET switch in parallel with said first MOSFET switch, a third source terminal of said third MOSFET switch being connected to said first source terminal, a third drain terminal of said third MOSFET switch being connected to said first drain terminal, and a third gate terminal of said third MOSFET switch being coupled to a gate signal, said gate signal being appropriately synchronized with said control signal, both said first MOSFET switch and said third MOSFET switch being in a conductive state so as to connect said source node to said destination node at substantially the same time in response to said control signal and said gate signal, respectively.

3. The output switch of claim 1 wherein said implantable medical device comprises a pacemaker having a stimulating lead adapted to be connected to a patient's heart, said pacemaker having means for storing an electrical charge of a desired magnitude, said storing means being electrically connected to said source node and said stimulating lead being electrically coupled to said destination node, whereby the output switch delivers the electrical charge stored in said storing means to said stimulating lead in response to said control signal.

4. In an implantable medical device having MOSFET connection means therein for selectively connecting a first node within said medical device to a second node within said medical device, said MOSFET connection means being formed on a semiconductor substrate of a first polarity type and having at least one well region therein of a second polarity type, and wherein source and drain terminals of said MOSFET connection means include regions of said first polarity type within said well region, and further wherein the structure of said MOSFET connection means includes regions of said first polarity type separated by a region of said second polarity type, thereby forming a parasitic bipolar transistor through which potentially large currents can flow, a means for maintaining said parasitic bipolar transistor in an OFF condition, thereby preventing any potentially large currents from flowing through said parasitic bipolar transistor, said means for maintaining said parasitic bipolar transistor in an OFF condition comprising:
    blocking means for preventing any electrical signals from being applied to a base terminal of said parasitic bipolar transistor in response to a blocking signal, said base terminal comprising the region of said second polarity type; and
    control means for generating said blocking signal and applying it to said base terminal whenever it is desired to maintain said parasitic bipolar transistor in an OFF condition.

5. The implantable medical device of claim 4 wherein said blocking means comprises a first switch that switchably connects the base terminal of said parasitic bipolar transistor to the first node of said medical device, said first node also being connected to one of said source and drain terminals of said MOSFET connection means, and wherein the other of said source and drain terminals of said MOSFET connection means is connected to the second node of said medical device, and further wherein said control means maintains said first switch in an open position in the presence of any signals appearing on the second node of said medical device that might otherwise turn said parasitic bipolar transistor ON.

6. The switch protection means of claim 5 wherein said first switch comprises a first MOSFET switch formed on the same semiconductor substrate as is used for said MOSFET connection means, said first MOSFET switch having a first of its source/drain terminals connected to the base of said parasitic bipolar transistor, a second of its source/drain terminals connected to the first node of said medical device, and its gate terminal coupled to the second node of said medical device, whereby any activating signal appearing on said second node, either from a source external to said medical device or from said first node through said MOSFET connection means, is also coupled to the gate terminal of said first MOSFET switch, said activating signal causing said first MOSFET switch to assume an OPEN state, thereby blocking any signals from being applied to the base of said parasitic bipolar transistor.

7. The switch protection means of claim 6 wherein said MOSFET connection means comprises a second MOSFET switch having its source and drain terminals connected to the first and second nodes of said medical device, and wherein both said first and second MOSFET switches comprise N-channel MOSFET devices formed on an N-type semiconductor substrate material, each N-channel MOSFET device having respective P-well terminals, the P-well terminal of said second MOSFET switch being electrically connected to the P-well terminal of said first MOSFET switch, and the P-well terminal of said first MOSFET switch being electrically connected to the base of said parasitic bipolar transistor.

8. Output switch means for use in an implantable medical device for selectively delivering an electrical stimulating pulse to an output terminal, said output switch means causing an electrical potential stored in a storage element of said medical device to be electrically connected to said output terminal for a select period of time in response to a trigger signal, said trigger signal being generated by control logic within said medical device, said output switch means comprising:

a first semiconductor switch having a first source terminal connected to said storage element, a first destination terminal connected to said output terminal, and a first control terminal coupled to said control logic, said control logic presenting said trigger signal to said first control terminal whenever a stimulation pulse is desired at said output terminal, said trigger signal causing said first source terminal to be electrically connected to said first destination terminal;

second semiconductor switch means for switchably connecting a supply potential to said output terminal in response to a turn-on potential, said second semiconductor switch means having a second source terminal coupled to the supply potential, a second destination terminal connected to said output terminal, and a second control terminal, said turn-on potential being applied to said second control terminal; and a third semiconductor switch having a third source terminal connected to the first source terminal of said first semiconductor switch, a third destination terminal connected to the second control terminal of said second semiconductor switch means, and a third control terminal, said third semiconductor switch being controlled so as to block the application of said turn-on potential to the second control terminal of said second semiconductor switch means.

9. The output switch means of claim 8 wherein said second semiconductor switch means comprises a bipolar transistor that undesirably results from the adjoining regions of doped semi-conductor material used to realize said first semiconductor switch.

10. The output switch means of claim 9 wherein said first and third semiconductor switches comprise N-channel MOSFET switches realized on a single N-type semiconductor substrate, each N-channel MOSFET switch having a P-well terminal associated therewith, the P-well terminal of said first N-channel MOSFET switch being electrically connected to the P-well terminal of the third N-channel MOSFET switch, this P-well connection also being electrically connected to the base of the bipolar transistor.

* * * * *